United States Patent [19]

Ishikawa et al.

[11] 4,446,738

[45] May 8, 1984

[54] ACOUSTIC SCANNING MICROSCOPE

[75] Inventors: Isao Ishikawa, Hino; Hiroshi Kanda, Tokorozawa; Kageyoshi Katakura, Tokyo, all of Japan

[73] Assignee: Hitachi, Ltd., Tokyo, Japan

[21] Appl. No.: 330,779

[22] Filed: Dec. 14, 1981

[30] Foreign Application Priority Data

Dec. 22, 1980 [JP] Japan .................... 55-180397

[51] Int. Cl.³ ............................................ G01N 29/04
[52] U.S. Cl. .................................... 73/606; 73/665
[58] Field of Search ............... 73/618, 606, 633, 665, 73/627; 248/631

[56] References Cited

U.S. PATENT DOCUMENTS 3,277,696 10/1966 Gertel .................................. 73/665
3,917,201 11/1975 Roll ................................... 248/631

OTHER PUBLICATIONS

Weglein, "Acoustic Microscopy Applied to Saw Dispersion and Film Thickness Measurement", *IEEE Transactions on Sonics and Ultrasonics*, vol. SU—27, No. 2, March 1980.

*Primary Examiner*—Anthony V. Ciarlante
*Attorney, Agent, or Firm*—Antonelli, Terry & Wands

[57] ABSTRACT

An acoustic scanning microscope includes a specimen table for supporting a specimen illuminated by an ultrasonic wave. The specimen table is supported in a non-contacting manner under aerostatic pressure or alternatively magnetic repulsion.

15 Claims, 6 Drawing Figures

ACOUSTIC SCANNING MICROSCOPE

BACKGROUND OF THE INVENTION

1. Field of the Invention

The present invention relates generally to an acoustic or ultrasonic microscope, and in more particular concerns an ultrasonic microscope which has a specimen table held in a contactless manner.

2. Description of the Prior Art

In recent years, generation and detection of acoustic waves at ultra high frequency of up to 1 GHz have succeeded with an acoustic wavelength of about 1 μm being made available in water. In reality, an ultrasonic imaging equipment of a high resolution has been realized for practical applications, in which a focused ultrasonic beam is generated with the aid of a concave lens system, allowing a resolution as high as 1 μm to be attained.

In an application of such ultrasonic imaging equipment, a specimen is inserted in an ultrasonic beam path, wherein an ultrasonic wave reflected by the specimen is detected and processed for studying elastic properties and the like of an extremely small area of the specimen. In another application, a specimen is scanned in two dimensions, wherein the resulting signals are displayed as brightness signals on a cathode-ray tube or CRT display with a desired magnification to facilitate observation of an extremely small given region of the specimen.

A typical one of the hitherto known acoustic microscope imaging equipments has been disclosed in U.S. Pat. No. 4,028,933. To have a better understanding of the invention, description will first be made in some detail on the prior art structure of such equipment.

Referring to FIG. 1 of the accompanying drawings which schematically illustrate a general structure of a probe or transducer system constituting a main part of a hitherto known ultrasonic microscope, an ultrasonic wave propagating medium 20 which may be a cylindrical crystal body of, for example, sapphire or silica glass has one end face 21 having a plane polished to an optical quality and the other end face which is formed with a concave semispherical hole 30. An RF pulse ultrasonic wave which is a plane wave is radiated into the crystal 20 by an RF pulse signal which is applied to a piezo-electric film 10 deposited on the end face 21. The plane ultrasonic wave is focused onto a specimen 50 located on a predetermined focal point through a positive acoustic lens formed at the interface between the semispherical hole 30 and a medium 40 which is usually water.

The ultrasonic wave reflected and scattered by the specimen 50 is collected and converted into a plane wave by means of the same lens. The plane wave is propagated through the interior of the crystal 20, and is finally converted into an RF electric signal by the piezo-electric film 10. The RF electric signal is detected by a diode circuit to be converted into a video signal, which is then utilized as the input signal of the CRT display mentioned above.

There are shown in FIG. 2 at (a) signal waveforms of a video frequency range produced in response to application of the RF pulse signal with a predetermined repetition rate $t_R$ in the hitherto known structure shown in FIG. 1. In FIG. 2, the abscissas represents a time axis while the intensity or magnitude of the signal is taken along the ordinate. A letter A designates the applied RF pulse, a letter B designates a reflected signal from the interface lens and a letter C designates a reflected signal from the specimen.

In order to discriminate the desired reflected signal C from the reflected signal B, the hitherto known imaging equipment adopts such an arrangement in which the duration $t_d$ (FIG. 2 (b)) of the impressed pulse is selected as short as possible so as to prevent the signals C and B from overlapping each other, whereby only the signal C is extracted through an appropriate timing gate operation, as illustrated in FIG. 2 at (c).

By the way, the resolution of such equipment includes an axial or depth resolution $\Delta\rho$ in the direction of propagation of the ultrasonic wave and a bearing resolution $\Delta\gamma$ in a plane extending in the direction perpendicular to the propagating direction of the ultrasonic wave. Both of these resolutions are determined by the wavelength $\lambda$ of the ultrasonic wave and the F number representative of the brightness of the lens as used, and are given by:

$$\Delta\gamma = \lambda \cdot F \quad (1)$$

$$\Delta\rho = 2\lambda \cdot F^2 \quad (2)$$

Since the F number of the lens which can be realized is on the order of 0.7, the resolutions $\Delta\gamma$ and $\Delta\rho$ will be, respectively, about 1 μm and 1.5 μm in the water (1,500 m/s) when the ultrasonic wave used is at 1 GHz.

For IC's or LSI's which are one of the most important objects to be examined by the ultrasonic microscope, more improved axial resolution is required, because layer patterns in the thicknesswise or depthwise direction of the specimen is often finer than a planar pattern, as is well known. In actuality, a typical IC has a multilayered structure composed of layers of 1 μm to 3 μm thick. With the axial resolution of 2 μm in the water as described above, it is utterly impossible to observe these layers independent of one another in a non-destructive manner with the position of a focal point set inwardly of the surface of the IC. This can be explained by the fact that, since the acoustic velocity is higher in a metal such as silicon and aluminum constituting the IC than in the water, the axial resolution is only from 4 to 10 μm even when the ultrasonic wave at 1 GHz is used.

SUMMARY OF THE INVENTION

An object of the present invention is to provide an acoustic or ultrasonic microscope having a specimen table which scarcely undergoes movements or vibrations in the vertical direction.

In view of the above object, it is proposed according to an aspect of the invention an acoustic or ultrasonic microscope provided with a specimen table which is held in place by aerostatic or magnetic force in a contactless manner.

DESCRIPTION OF THE PREFERRED EMBODIMENTS

Figure 1:
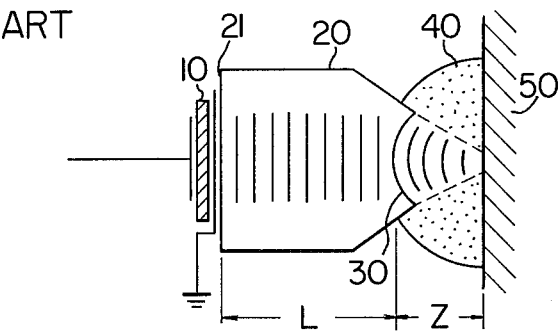
FIG. 1 is a view to illustrates a probe or transducer system of a conventional acoustic microscope.

In U.S. patent application Ser. No. 261,032 filed in the name of the inventors of the present application, thre is disclosed an acoustic microscope which was developed with a view to eliminating the shortcomings of the prior art acoustic microscope described hereinabove in conjunction with FIG. 1 and exhibits an improved axial resolution.

Figure 2:
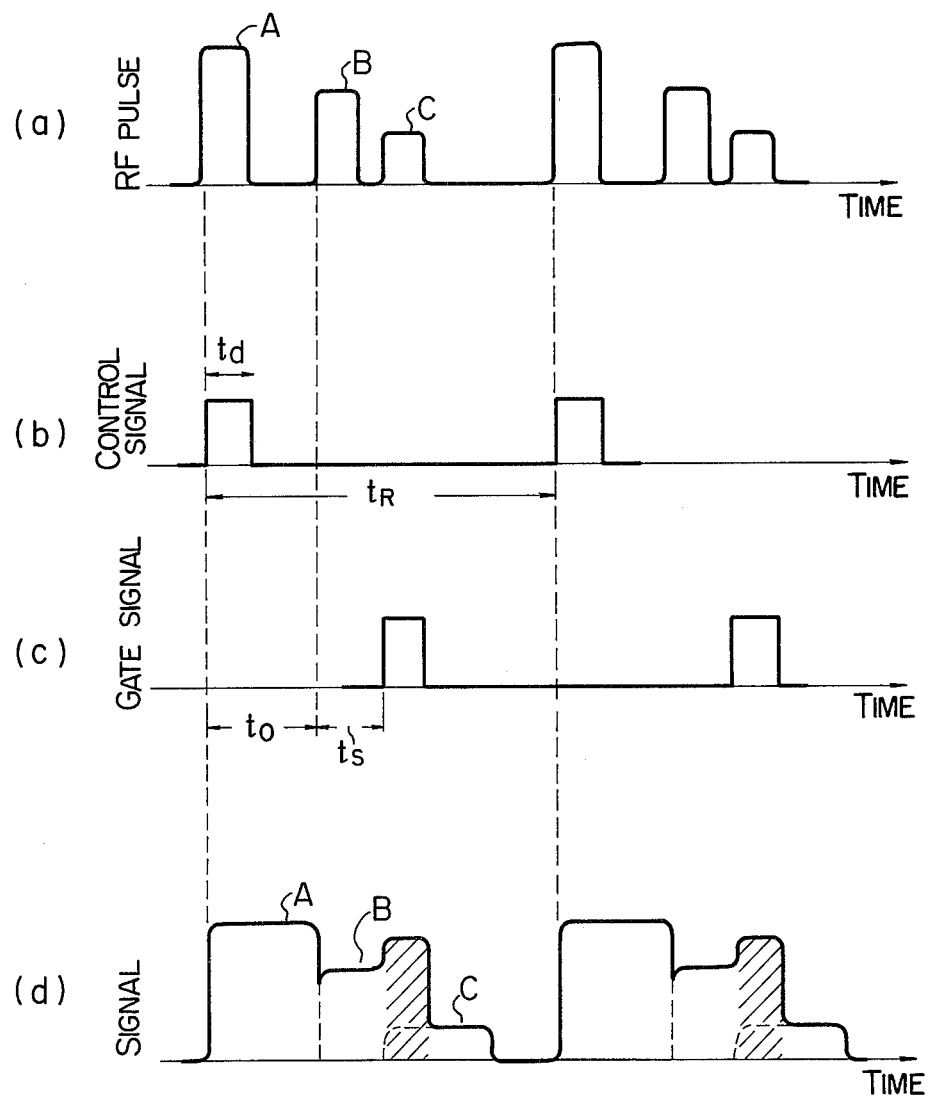
FIG. 2 shows signal timing diagrams to illustrate the principle of an interference type acoustic microscope.

The principle of the acoustic microscope proposed in the above application is illustrated in FIG. 2 at (d). According to this principle, reflected ultrasonic signal C from a specimen is caused to interfere with a reflected ultrasonic signal B from the interface between a lens and water by increasing the duration $t_d$ of the RF pulse, in contrast to the case of the prior art.

More particularly, when compared with the reflected signal B from the interface between the lens and the water, the reflected ultrasonic signal C from the specimen returns with a delay time equal to a time interval $2Z/V_w$ (where Z represents a space or distance between the lens and the specimen, and $V_w$ represents the sound velocity in the water) which is required for the ultrasonic wave propagates reciprocatively in the water between the lens and the specimen. Accordingly, when the duration $t_d$ of the RF pulse is made longer such that $$t_d > 2Z/V_w (= t_s) \tag{3}$$

the two reflected signals mentioned above come to overlap each other. The interference of the two reflected signals can be detected in such a way that the signals in a time range in which they overlap each other are taken out through a timing gate operation.

More specifically, it is assumed that the reflected signal B from the interface between the lens and the water is expressed as follows:

$$V_B(t) = A \sin w_o t \tag{4}$$

where $t_o < t < t_o + t_d$, and where $w_o$ represents the frequency of the ultrasonic wave used, and $t_o = 2L/V_L$ in which L represents the length of the lens and $V_L$ represents the acoustic velocity in the material of the lens. Then, the reflected ultrasonic signal C from the specimen is expressed as follows:

$$V_C(t) = B \sin w_o(t + 2Z/V_w) \tag{5}$$

where $t_o + t_s < t < t_o + t_s + t_d$. Thus, it can be seen that the two signals overlap under the condition of the expression (3) and that expression of $V(t) = A \sin w_o t + B \sin w_o(t + 2Z/V_w)$ [hatched region in FIG. 2 at (d)] becomes valid for a time duration defined as follows:

$$t_o + t_s < t < t_o + t_d \tag{6}$$

When these signals are subjected to the square law detection with a diode circuit, a signal of a video frequency is derived, which can be expressed as follows:

$$V(t) = A^2 + B^2 + 2 A B \cos\left(w_o \frac{2Z}{V_w}\right) \tag{7}$$

When the time relation defined by the expression (6) is considered, the following relation holds:

$$w_o \frac{2Z}{V_w} = 2\pi Z/(\lambda/2) \tag{8}$$

Thus, when the distance Z between the lens and the specimen is varied, the detection signal is correspondingly modulated at a period of $\lambda/2$. In other words, it is possible to detect the unevenness pattern of the surface of the specimen or the internal layer patterns of the specimen at a resolution of approximately $\lambda/5$ (modulation degree: 50%). This value $\lambda/5$ corresponds to the axial resolution $\lambda$ (provided that F=0.7) in the hitherto known method. It will be appreciated that the resolution is improved by a factor of 5 according to the interference method proposed in the U.S. application cited above. More specifically, when the ultrasonic wave of 1 GHz is used in the hitherto known method, the axial resolution in the water was only on the order of 1.5 μm and it was 8.4 μm in silicon (8,400 m/s), whereas according to the interference method described above, it is possible to attain the axial resolution of 0.3 μm in water and 1.7 μm in silicon, to a significant improvement over the hitherto known acoustic microscope, and permits the observation of the individual layers of the multilayered structure of IC.

As will be appreciated from the foregoing description, it is possible to improve the axial resolution of the ultrasonic microscope by adopting the acoustic interference method disclosed in U.S. application cited above. However, in order to further enhance the axial resolution of the ultrasonic microscope, it is required that a specimen should scarcely undergo movements or vibrations in the vertical or axial direction. For example, it has been experimentally confirmed that the permissible movements of the specimen in the vertical direction should be on the order of one tenth of the axial resolution, say about 0.03 μm. However, in the arrangement of the hitherto known microscope in which the specimen is scanned two-dimensionally through mechanical means, difficulty is encountered in attaining the permissible or tolerance value mentioned above, because the specimen table can not be manipulated in a stable manner as required, because of unevenness of bearing members, non-uniform contact or the like cause of the hitherto known bearing or supporting system for the specimen table.

Accordingly, with the present invention, it is contemplated to provide a specimen table which is so arranged as to be supported in a contactless manner, thereby to further improve the axial resolution of the ultrasonic microscope.

Figure 3:
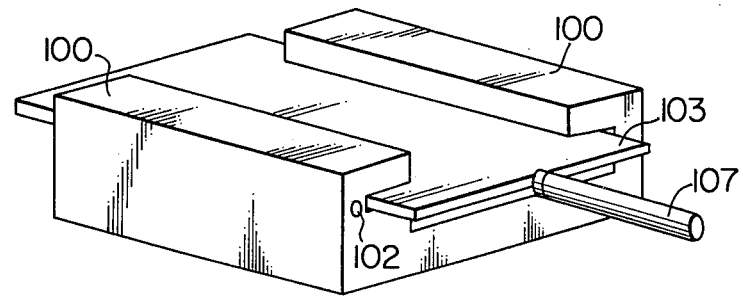
FIG. 3 is a perspective view showing a structure according to an exemplary embodiment of the invention.
Figure 4:
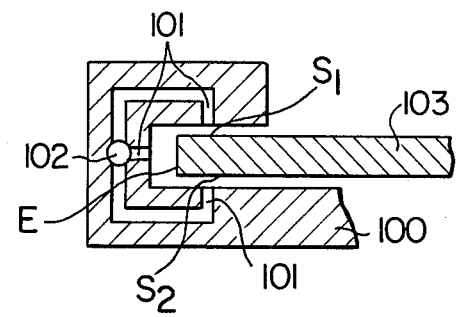
FIG. 4 is a fragmental enlarged sectional view of the same.

Referring to FIGS. 3 and 4 which shows a structure of supporting means for supporting a specimen table of an ultrasonic microscope in a contactless manner according to an exemplary embodiment of the present invention and in which FIG. 3 shows the supporting structure in a perspective views, while FIG. 4 shows the same in a fragmental sectional view as seen in the direction of an arrow, a compressed air stream is caused to flow through spaces between the specimen table and supporting or bearing members disposed at both sides and the ends of the specimen table so that the specimen table is supported under an aerostatic force or pressure. With this structure, there is produced practically no frictional resistance between the specimen table and the supporting and guiding members, involving no abrasion in any parts. Further, by virtue of the fact that the aerostatic flow layer serves as a buffer, the specimen table can moved smoothly even when small roughnesses or irregularities are present in the opposite surfaces of the supporting guide portions and the specimen table.

In FIGS. 3 and 4, the supporting guide portions are denoted by a numeral 100 and is provided with compressed air discharge passage 101 at predetermined positions for supporting the specimen table 103 at the oppositely facing side surface portions $S_1$ and $S_2$ as well as the lateral end surface portion E thereof. The specimen table is held in place by the compressed air flows discharged from the compressed air discharge passage 101. A reference numeral 102 denotes a compressed air intake port, and 107 denotes a driving shaft for the specimen table.

With the specimen table structure described above, it has been experimentally ascertained that the movement of a specimen in the vertical direction can be restricted within a limit of less than 0.03 μm, whereby an acoustic microscope having a further improved axial resolution can be realized.

In the case of the embodiment shown in FIGS. 3 and 4, the supporting guide portions and the specimen table are supported in the non-contacting manner under the aerostatic force produced by the compressed air flow in the space between the opposite surfaces of the supporting guide portions and the specimen table. However, a magnetic repulsion may also be made use of for supporting the specimen table in the non-contacting manner.

Figure 5:
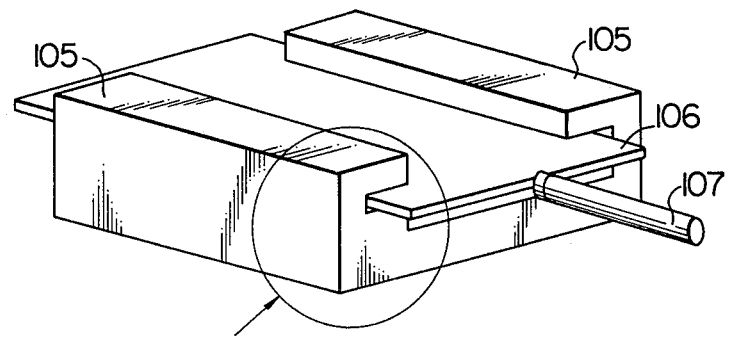
FIG. 5 is a perspective view illustrating another embodiment of the invention.
Figure 6:
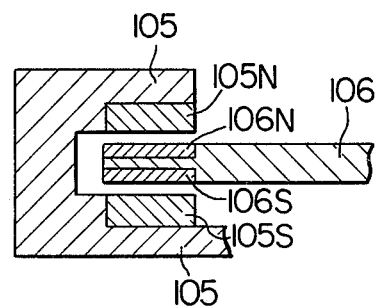
FIG. 6 is a sectional view of the same.

A specimen table supporting structure in which magnetic repulsion is made use of is exemplarily illustrated in FIGS. 5 and 6, in which FIG. 5 shows the same in a perspective view while FIG. 6 shows in an enlarged fragmental sectional view as seen in the direction indicated by an arrow. In particular, referring to FIG. 6, there are provided in each of guide portions 105 magnetic pole pieces 105N and 105S of opposite polarities in opposition to each other. Each of edge portions of the specimen table 106 which is adapted to be movably accommodated in each of the guide portions 105 is also provided with a pair of upper and lower magnetic pole pieces 106N and 106S of opposite polarities so as to face in opposition to the pole shoe members 105N and 105S of the guide member 105, respectively. In this manner, the specimen table 106 is held or supported without any physical contact with the supporting guide portions 105 under the influence of the magnetic repulsing force acting between the opposite pole pieces 105N and 106N as well as between the opposite pole pieces 105S and 106S of the guide 105 and the table 106, respectively.

The manner in which the specimen table is supported by making use of the magnetic forces in the structure shown in FIGS. 5 and 6 is similar to the case of the structure in which the specimen table is aerostatically held as described hereinbefore by referring to FIGS. 3 and 4. The specimen table 103 is connected to a driving shaft 107 to be periodically reciprocated for scanning a specimen placed on the table 103.

It will now be appreciated that the present invention now provided an ultrasonic microscope, and in particular an interference type ultrasonic microscope provided with a specimen table which is supported in a non-contacting and friction-free manner and undergoes practically no movements in the vertical direction.

We claim:

1. In an acoustic microscope comprising an acoustic wave propagating medium, a piezo-electric element formed at one end of said acoustic wave propagating medium, and an acoustic wave lens formed at the other end of said propagating medium and having a focal point at a predetermined position, wherein an image of a specimen located at said focal point is produced on the basis of the acoustic wave disturbed by said specimen, an improvement comprising supporting means for supporting a specimen table for said specimen in a non-contacting manner, said table having oppositely facing side surfaces, said supporting means being constituted by bearing members for supporting said specimen table under aerostatic pressure at least at portions along the oppositely facing side surfaces.

2. An acoustic microscope according to claim 1, wherein said supporting means further comprises at least one bearing member for supporting said specimen table at an end thereof under aerostatic pressure.

3. In an acoustic microscope comprising an acoustic wave propagating medium, a piezo-electric element formed at one end of said acoustic wave propagating medium, and an acoustic wave lens formed at the other end of said propagating medium and having a focal point at a predetermined position, wherein an image of a specimen located at said focal point is produced on the basis of the acoustic wave disturbed by said specimen, an improvement comprising supporting means for supporting a specimen table for said specimen in a non-contacting manner, said table having oppositely facing side surfaces, said supporting means being constituted by bearing members for supporting said specimen table under magnetic repulsing forces at least at portions along the oppositely facing side surfaces.

4. In an acoustic microscope comprising an acoustic wave propagating medium, a piezo-electric element formed at one end of the acoustic wave propagating medium, and an acoustic wave lens formed at the other end of the propagating medium and having a focal point at a predetermined position, wherein an image of a specimen located at the focal point is produced on the basis of the acoustic wave disturbed by the specimen, the specimen being supportable on a specimen table having oppositely facing side surfaces, the improvement comprising supporting means for non-contactingly supporting the specimen table for the specimen, the supporting means non-contactingly supporting the specimen table at least at portions along the oppositely facing side surfaces thereof.

5. An acoustic microscope according to claim 4, wherein the supporting means further non-contactingly supports the specimen table along a lateral end surface thereof.

6. An acoustic microscope according to claim 4, wherein the oppositely facing side surfaces of the specimen table are upper and lower side surfaces, the supporting means comprising bearing means for supporting the specimen table at the upper and lower side surfaces under aerostatic pressure.

7. An acoustic microscope according to claim 6, wherein the supporting means comprises additional bearing means for additionally supporting the specimen table at a lateral end surface thereof under aerostatic pressure.

8. An acoustic microscope according to claim 4, wherein the supporting means comprises bearing means for supporting the specimen table along the oppositely facing side surfaces under magnetic repulsive forces.

9. An acoustic microscope according to claim 8, wherein the oppositely facing side surfaces of the specimen table are upper and lower side surfaces thereof.

10. An acoustic microscope according to claim 4, wherein the supporting means comprises means cooperating with the oppositely facing side surfaces of the specimen table for supporting and restricting movement of the specimen table in a direction transverse to the oppositely facing side surfaces thereof.

11. An acoustic microscope according to claim 10, wherein the specimen table is arranged for movement in a direction extending in a plane of the oppositely facing side surfaces.

12. An acoustic microscope according to claim 11, wherein the supporting means comprises bearing means for directing a pressurized fluid onto the oppositely facing side surfaces of the specimen table.

13. An acoustic microscope according to claim 11, wherein the supporting means comprises additional bearing means for directing a pressurized fluid onto a lateral end surface of the specimen table.

14. An acoustic microscope according to claim 11, wherein the supporting means comprises bearing means for providing magnetic repulsive forces between a support member for the specimen table and the oppositely facing side surfaces of the specimen table.

15. An acoustic microscope according to claim 14, wherein the support member is provided with at least a first magnetic member of one polarity and one of the oppositely facing side surfaces of the specimen table is provided with a first magnetic member of the one polarity for cooperating with the first magnetic member of the support member to provide a magnetic respulsive force therebetween, the support member being provided with at least a second magnetic member of an opposite polarity and the other of the oppositely facing side surfaces being provided with a second magnetic member of the opposite polarity for cooperating with the second magnetic member of the support member to provide a magnetic repulsive force therebetween.

* * * * *